United States Patent [19]

Beetz

[11] Patent Number: 4,661,522
[45] Date of Patent: Apr. 28, 1987

[54] CYCLOALKANE-INDENE-CARBOXIMIDA-MIDE DERIVATIVES

[75] Inventor: Tom Beetz, Lith, Netherlands

[73] Assignee: Akzo N.V., Arnhem, Netherlands

[21] Appl. No.: 734,049

[22] Filed: May 15, 1985

[30] Foreign Application Priority Data

May 24, 1984 [NL] Netherlands .......................... 8401653
May 25, 1984 [NL] Netherlands .......................... 8401670

[51] Int. Cl.$^4$ .................. A61K 31/155; C07C 123/00
[52] U.S. Cl. .................................... 514/632; 564/226; 564/229; 564/244; 514/633; 514/637
[58] Field of Search ................ 564/229, 226, 244; 514/632, 633, 637

[56] References Cited

U.S. PATENT DOCUMENTS 4,499,105 2/1985 Panneman .......................... 564/229

OTHER PUBLICATIONS

Vejdelek, Z. J. et al. Collection Czech. Chem. Commun., vol. 41, (1976), pp. 2020-2033.

*Primary Examiner*—Natalie Trousof
*Attorney, Agent, or Firm*—Wegner & Bretschneider

[57] ABSTRACT

The present invention is dealing with cycloalkane-indene-carboximidamide derivatives having the general formula:

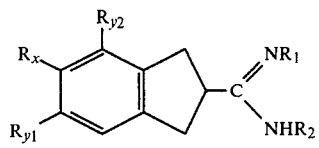

wherein
$R_x$ together with either $R_{y1}$ or $R_{y2}$ represent the moiety

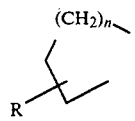

(the other Ry being hydrogen),
n represents the number 1, 2 or 3,
R represents hydrogen or a (1-4 C)-alkyl group,
$R_1$ represents hydrogen, (1-4 C)-alkyl, hydroxyl, (1-4 C)-alkoxy or an amino group which is unsubstituted or substituted by (1-4 C)-alkyl and
$R_2$ is hydrogen, hydroxyl or (1-4 C)-alkyl,
as well as the pharmaceutically acceptable salts thereof, with powerful blood platelet aggregation-inhibiting activity.

5 Claims, No Drawings

CYCLOALKANE-INDENE-CARBOXIMIDAMIDE DERIVATIVES

The present invention is dealing with cycloalkane-indene-carboximidamide derivatives and to a pharmaceutical preparation which contains these novel compounds as the active constituent.

More especially, the invention relates to carboximidamide derivatives having the general formula:

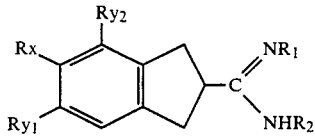

wherein:
Rx together with either Ry$_1$ or Ry$_2$ represent the moiety

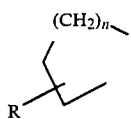

(the other Ry being hydrogen),
n represents the number 1, 2 or 3,
R represents hydrogen or a (1–4 C)-alkyl group,
R$_1$ represents hydrogen, (1–4 C)-alkyl, hydroxyl, (1–4 C)-alkoxy or an amino group which is unsubstituted or substituted by (1–4 C)-alkyl and
R$_2$ is hydrogen, hydroxyl or (1–4 C)-alkyl, as well as the pharmaceutically acceptable salts thereof.

The present compounds and salts thereof exhibit powerful blood platelet aggregation-inhibiting activity, as a result of which they are useful in combating certain cardiovascular conditions. They have relatively few side-effects.

The compounds according to the general formula I can be prepared in a manner usual for analogous compounds.

The compounds I can, for example, be prepared by condensing a O- or S-alkyliso(thio)amide having the general formula II:

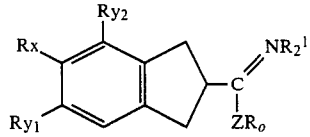

or an acid addition salt thereof, with ammonia or a hydroxylamine, hydrazine or amine derivative having the formula III:

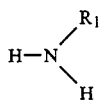

or an acid addition salt thereof, wherein Rx, Ry$_1$, Ry$_2$, R, n and R$_1$ have the meanings given above, R$_2^1$ has the same meaning as R$_2$ but can also be an amino group which is unsubstituted or substituted by (1–4 C)-alkyl, Z represents an oxygen or sulphur atom and R$_o$ represents a lower alkyl group, preferably methyl or ethyl.

The compounds I wherein R$_2$ represents hydrogen or hydroxyl can moreover be prepared by condensation of the nitrile of the general formula IV:

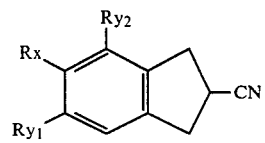

wherein Rx, Ry$_1$ and Ry$_2$ have the above-mentioned meaning, with a compound of the general formula III described above, or an acid addition salt thereof.

The starting materials of the general formulae II and IV required for the above condensation reactions can be prepared in a manner customary for analogous compounds.

Compounds according to the general formula III needed in the above-mentioned condensation reactions include, inter alia, ammonia (NH$_3$), methylamine, ethylamine, propylamine, isobutylamine, butylamine, hydroxylamine, hydroxylamine methyl ether, hydroxylamine ethyl ether, hydroxylamine propyl ether, hydrazine, 1-methylhydrazine and 1,1-dimethylhydrazine, as well as the acid addition salts thereof.

Preferably, the substituents on the nitrogen atoms (R$_1$, R$_2$) should already be present in either starting material mentioned.

However, it is also possible to modify or introduce one or more substituents after the above-mentioned condensation reactions.

For example, one of the nitrogen atoms of a compound I (R$_1$ or R$_2$=H) can be alkylated in a known manner, for example by means of alkyl halides, by means of an Eschweiler-Clarke reaction or by acylation followed by reduction. The N-hydroxyl group which may be present in the compound of formula I (R$_1$ or R$_2$ is hydroxyl) will also be alkylated during such an alkylation. Moreover, this N-hydroxyl group can be specifically alkylated by means of, for example, dimethyl sulphate.

The compounds of the formula I contain an alkaline group. They can, depending on the medium in which they are prepared, be obtained as free base or as an acid addition salt. However, if desired the free base I can be prepared from the salt, for example by reaction with an alkaline compound or by means of an ion exchanger, while the free base I can be converted in a simple manner into an acid addition salt.

Pharmaceutically acceptable acid addition salts are obtained by allowing the free base I to react with acids, such as hydrochloric acid, phosphoric acid, acetic acid, propionic acid, glycolic acid, maleic acid, fumaric acid, malonic acid, succinic acid, tartaric acid, lactic acid, citric acid, ascorbic acid or salicylic acid.

It follows from the general formula I of the end products that the compounds according to the invention may contain an asymmetric carbon, as a result of which not only racemic mixtures I but also optically active compounds I are possible. These optically active compounds I are also to be included among the compounds according to the invention. They can be prepared directly from an optically active starting material (II, IV) or be obtained by resolving the racemate I into its optical antipodes in a manner customary for such resolutions.

The present compounds according to the invention can be administered orally, locally or parenterally, preferably in a daily dose of between 0.01 and 50 mg per kilogram of body weight. The compounds are, for this purpose, converted in a customary manner into a form suitable for oral, local or parenteral administration, for example a tablet, pill, capsule, solution, suspension, emulsion, paste or spray.

An administration form for oral use is preferred.

Compounds I which are preferred are compounds wherein the carboximidamide group has the following structures:

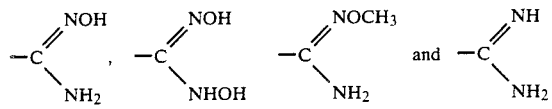

More especially that compound of formula I is preferred wherein R represents hydrogen, n represents the number 1 or 2, $R_2$ is hydrogen and $R_1$ represents a hydroxyl group, as well as acid addition salts thereof.

The position of the double bond between the nitrogen and carbon atom in the carboximidamide group of formula I cannot be specified unambiguously since an equilibrium will set up between the groups:

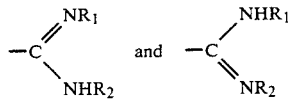

Both tautomeric forms are included in the invention.

Preparation of starting materials

A. Ethyl 2-cyano-2,3,5,6,7,8-hexahydro-1H-benz[f]indene-2-carboxylate $NaOC_2H_5$ was prepared in a 10 liter 3-necked flask by adding small pieces of sodium (1.68 moles) to absolute ethanol (900 ml) over a period of about 1 hour. The temperature was kept at 60°–70° C. by controlling the speed of addition.

After all sodium had reacted, the mixture was cooled to room temperature and thereafter dry THF (1650 ml) and ethyl cyanoacetate (1.68 moles) were added all at once. After 5 minutes, a precipitate began to form and slowly thickened. After 30 minutes' stirring, the reaction mixture was cooled with ice water to 10°–15° C. and thereafter a solution of 2,3-bis-(bromoethyl)-5,6,7,8-tetrahydro-naphthalene (0.84 mole) in dry THF (1000 ml) was added as rapidly as possible (2 to 3 minutes). As a result of the exothermic character of the reaction, the temperature rose to about 35° C.; thereafter the mixture was cooled to room temperature and stirred for a further hour.

The reaction mixture was then evaporated as far as possible and the residue was partitioned between methylene chloride (750 ml) and water (about 400 ml). The layers were separated and the water layer was extracted twice with methylene chloride (250 ml). The combined methylene chloride extracts were washed once with water (200 ml) and dried over $Na_2SO_4$. After the drying agent had been filtered off, the filtrate was evaporated. This gave about 300 g of a yellow oil.

300 ml of ether were added to the residue and after seeding 80.5 g of the desired compound crystallised out.

B. 2,3,5,6,7,8-Hexahydro-1H-benz[f]indene-2-carbonitrile

The product (0.29 mole) obtained in A. was suspended in DMSO (160 ml). Distilled water (12 ml) and iodine-free sodium chloride (5.6 g) were added. Thereafter the reaction mixture was heated to 170° C. for about 3 hours, with stirring, until the $CO_2$ evolution had ceased.

After it had cooled to room temperature, the reaction mixture was poured out slowly, with stirring, into distilled water (1000 ml). The precipitate was extracted with methylene chloride (4×200 ml) and the combined extracts were washed with water (200 ml), dried over $Na_2SO_4$ and evaporated. The residue was filtered over silica gel. Melting point 102° C.

C. In a corresponding manner as described in A. and B. was prepared:

2,3,4,5,6,7-hexahydro-1H-benz[e]indene-2-carbonitrile; m.p. 48° C.

EXAMPLE 1

2,3,5,6,7,8-Hexahydro-N-hydroxy-1H-benz[f]indene-2-carboximidamide.HCl 29.2 g of sodium were dissolved in 560 ml of dry methanol and a warm solution of 88 g of hydroxylamine hydrochloride in 110 ml of dry methanol was thereafter added to this solution. The solution obtained had a pH of 8 to 10. Thereafter, the NaCl precipitate formed was filtered off.

The filtrate obtained was added at room temperature, under nitrogen, to a solution of 25 g (127 millimoles) of 2,3,5,6,7,8-hexahydro-1H-benz[f]indene-2-carbonitrile in 560 ml of dry methanol.

The reaction mixture was stirred for 3×24 hours at 50° C. under nitrogen and was then evaporated.

The residue was thereafter stirred with 400 ml of water, after which the precipitate was filtered off, again washed with water and dried. Yield 28 g.

The precipitate was then dissolved in 120 ml of 5N methanolic HCl solution. The solution was evaporated to a volume of about 100 ml after which 250 ml of diethyl ether were added.

The precipitate formed after some time at 0° C. was filtered off and dried.

Yield: 26 g of the compound shown in the title.

Rf in methylene chloride:methanol (9:1)=0.44 on $SiO_2$; melting point: 213° C. (with decomposition).

EXAMPLE 2

The following are prepared in a manner analogous to Example 1:

2,3,5,6,7,8-hexahydro-N-hydroxy-6-methyl-1H-benz[f]indene-2-carboximidamide.HCl, melting point 205° C. (with decomposition);

1,2,3,5,6,7-hexahydro-N-hydroxy-s-indacene-2-carboximidamide.HCl, melting point: 215° C. (with decomposition);

1,2,3,5,6,7-hexahydro-N-hydroxy-6-methyl-s-indacene-2-carboximidamide.HCl, melting point: 194°–195° C.;

1,2,3,5,6,7,8,9-octahydro-N-hydroxy-cyclohept[f]indene-2-carboximidamide;

2,3,4,5,6,7-hexahydro-N-hydroxy-1H-benz[e]indene-2-carboximidamide.HCl, melting point: 194° C. (dec.);

2,3,4,5,6,7-hexahydro-N-hydroxy-5-methyl-1H-benz[e]indene-2-carboximidamide.HCl;

1,2,3,4,5,6-hexahydro-N-hydroxy-as-indacene-2-carboximidamide.HCl;

1,2,3,4,5,6-hexahydro-N-hydroxy-6-methyl-as-indacene-2-carboximidamide.HCl;

1,2,3,4,5,6,7,8-octahydro-N-hydroxy-cyclohept[e]indene-2-carboximidamide.

EXAMPLE 3

2,3,5,6,7,8-Hexahydro-N-methoxy-1H-benz[f]indene-2-carboximidamide.HCl

Method A

A sodium methanolate solution prepared by dissolving 3.45 g (150 millimoles) of sodium in 50 ml of methanol, was added to a solution of 12.5 g (150 millimoles) of hydroxylamine methyl ether hydrochloride in 60 ml of methanol.

After the mixture had been stirred for about 5 minutes, the sodium chloride formed was filtered off and the filtrate was added to 10 g (50 millimoles) of 2,3,5,6,7,8-hexahydro-1H-benz[f]indene-2-carbonitrile.

After 15 hours' stirring at 50° C., the methanol was removed and the residue was stirred with 250 ml of water.

After the precipitate had been filtered off, washed neutral with water and dried to constant weight, the amidoxime was suspended in 35 ml of methanol and acidified with 2N methanolic HCl solution.

After addition of 165 ml of ether to the solution, the hydrochloride crystallised out. Yield 10.6 g.

Method B 0.5 ml of water, 0.53 g (2 millimoles) of 2,3,5,6,7,8-hexahydro-N-hydroxy-1H-benz[f]indene-2-carboximidamide hydrochloride and, after a few minutes' stirring, 0.3 ml (about 3 millimoles) of dimethyl sulphate, were added successively to a solution of 92 mg 4 millimoles) of sodium in 5 ml of ethanol.

After the mixture had been stirred for 1 hour at room temperature, 2 millimoles of sodium ethanolate solution and 0.2 ml (0.2 millimole) of dimethyl sulphate were furthermore added.

After this mixture had been stirred for some time at room temperature, the solvent was evaporated off. The residue was then taken up in ethyl acetate and washed 3 times with water. The organic layer was dried over sodium sulphate and then evaporated to dryness, and the residue was subsequently converted to the hydrochloric acid salt by suspending it in 3 ml of methanol and acidifying with 2N methanolic HCl.

Addition of 3 ml of ether to the solution caused the hydrochloride to crystallise out. Yield 355 mg.

EXAMPLE 4

2,3,5,6,7,8-Hexahydro-N,N'-dihydroxy-1H-benz[f]indene-2-carboximidamide.

Small portions of about 7.5 millimoles of a sodium methanolate solution were added, with stirring, to a suspension of 10 g (50 millimoles) of 2,3,5,6,7,8-hexahydro-1H-benz[f]indene-2-carbonitrile and 10.5 g (150 millimoles) of hydroxylamine hydrochloride in 80 ml of methanol, at 45° C. In total, about 40 millimoles of sodium methanolate were used, spread over 48 hours.

After the mixture had cooled to room temperature, 80 ml of ether were added and the precipitate was filtered off. This precipitate was subsequently stirred twice with 50 ml of water to remove salts, and was then recrystallised from methanol/ether. Yield 7.0 g, melting point 151° C.

EXAMPLE 5

2,3,5,6,7,8-Hexahydro-N-hydroxy-1H-benz[f]indene-2-carboximidamide.HCl

A solution of 20.3 millimoles of 2,3,5,6,7,8-hexahydro-1H-benz[f]indene-2-carbonitrile in 16 ml of methylene chloride and 6 ml of ethanol was saturated with HCl gas at 0° C. After leaving the mixture in a refrigerator for 24 hours, the solvents were removed and the iminoethyl ether hydrochloride was dissolved in 100 ml of water. This solution was treated with a sodium bicarbonate solution and then extracted with methylene chloride, and the organic layer was washed with water until neutral. Thereafter, the solvent was removed.

To this residue (iminoethyl ether) there was subsequently added a hydroxylamine solution which was prepared by adding a solution of 120 millimoles of sodium in 10 ml of methanol to 120 millimoles of hydroxylamine hydrochloride in 10 ml of methanol. After 45 minutes' stirring at room temperature, the solvent was removed and the residue was stirred with water.

The precipitate was filtered off, washed neutral with water and dried to constant weight, giving 3.5 g of amidoxime.

A suspension of this amidoxime in 20 ml of methanol, when acidified with 2N methanolic HCl, gave a solution of the hydrochloride which after concentration to about 20 ml and addition of 150 ml of ether started to crystallise. Yield 3.9 g, melting point 213° C. (with decomposition).

EXAMPLE 6

2,3,5,6,7,8-Hexahydro-1H-benz[f]indene-2-carboximidamide.HCl 4 g (20.3 millimoles) of 2,3,5,6,7,8-hexahydro-1H-benz[f]indene-2-carbonitrile were converted to the corresponding iminoethyl ether in the same manner as described in Example 5.

The residue obtained (iminoethyl ether) was dissolved in 14 ml of dry methanol, after which 1.03 g of NH₄Cl were added.

The reaction mixture was then stirred for some time at 40° C. and then set aside at room temperature for 24 hours.

After the mixture had been evaporated and chromatographed with methylene chloride:methanol (1:1) as eluent over a short silica gel column, it was acidified with ethanolic HCl solution and again evaporated. The residue was recrystallised from ethanol:ether (1:3). Yield 3.7 g, melting point 279° C. (dec.).

EXAMPLE 7

The following compounds are prepared in a corresponding manner to that described in Example 6:

1,2,3,5,6,7-hexahydro-s-indacene-2-carboximidamide.HCl, melting point 282° C. (dec.);

2,3,4,5,6,7-hexahydro-1H-benz[e]indene-2-carboximidamide.HCl, melting point 222° C. (dec.).

In an analogous manner as described in Example 6 but replacing ammoniumchloride by methylamine the following compounds are prepared:

2,3,5,6,7,8-hexahydro-N-methyl-1H-benz[f]indene-2-carboximidamide;

2,3,4,5,6,7-hexahydro-N-methyl-1H-benz[e]indene-2-carboximidamide.

EXAMPLE 8

2,3,5,6,7,8-Hexahydro-N-hydroxy-N'-methyl-1H-benz[f]indene-2-carboximidamide 720 mg of a 60% dispersion of sodium hydride in oil (18 millimoles of sodium hydride) were freed from the oil with hexane after which 13 ml of dimethylformamide were added, followed by 1.3 g (18 millimoles) of hydroxylamine hydrochloride added over 20 minutes. The mixture was stirred for 20 minutes, the precipitate was filtered off, and the filtrate was added to 3.5 g (9 millimoles) of methyl-2,3,5,6,7,8-hexahydro-N-methyl-1H-benz[f]indene-2-carboximidothioate hydriodide.

The reaction mixture was stirred for a further 45 minutes at room temperature, poured out into 600 ml of water and brought to pH 9 with 4N sodium hydroxide, after which the precipitate formed was filtered off and washed neutral. Drying to constant weight gave 1.8 g of the carboximidamide in question, melting point 161° C.

The following compounds are prepared in an analogous manner but using hydrazine hydrate in place of hydroxylamine hydrochloride:

2,3,5,6,7,8-Hexahydro-N-amino-N'-methyl-1H-benz[f]indene-2-carboximidamide;

2,3,4,5,6,7-hexahydro-N-amino-N'-methyl-1H-benz[e]indene-2-carboximidamide.

What is claimed is:

1. A compound of the formula:

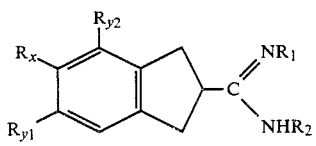

wherein

Rx together with either Ry1 or Ry2 represent the moiety

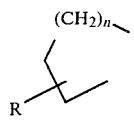

(the other Ry being hydrogen), n represents the number 1, 2 or 3,

R represent hydrogen or a (1–4 C)-alkyl group,

R1 represents hydrogen, (1–4 C)-alkyl, hydroxyl, (1–4 C)-alkoxy or an amino group which is unsubstituted or substituted by (1–4 C)-alkyl and R2 is hydrogen, hydroxyl or (1–4 C)-alkyl, as well as the pharmaceutical acceptable salts thereof.

2. Compound according to claim 1 of the formula:

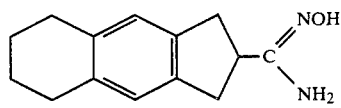

and pharmaceutically acceptable salts thereof.

3. Compound according to claim 1 of the formula:

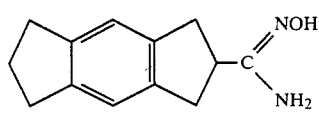

and pharmaceutically acceptable salts thereof.

4. Compound according to claim 1 of the formula:

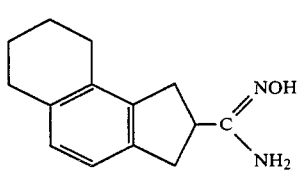

5. A pharmaceutical composition having blood platelet aggregation-inhibiting activity comprising
  a blood platelet aggregation-inhibiting effective amount of a compound of claim 1 and
  a pharmaceutically acceptable carrier therefore.

* * * * *